United States Patent [19]

Garris

[11] Patent Number: 4,770,166
[45] Date of Patent: Sep. 13, 1988

[54] ELLIPTICAL FINGER RING SPLINT

[76] Inventor: Cynthia G. Garris, P.O. Box 1063, Charlottesville, Va. 22902

[21] Appl. No.: 927,444

[22] Filed: Nov. 6, 1986

[51] Int. Cl.⁴ .............................................. A61F 5/10
[52] U.S. Cl. .................................... 128/77; 128/87 A
[58] Field of Search ...................... 128/87 A, 77, 87 R

[56] References Cited

U.S. PATENT DOCUMENTS

| | | | |
|---|---|---|---|
| 3,170,460 | 2/1965 | Stilson | 128/77 |
| 4,270,528 | 6/1981 | Hanson | 128/87 A X |
| 4,297,992 | 11/1981 | LaRue et al. | 128/87 A X |

OTHER PUBLICATIONS

"Arthritis Rational Therapy and Rehabilitation", Robert L. Swezey, 1978.
"Arthritis and Rheumatism", Robert L. Bennett, Oct. 1965.
"Clinics in Rheumatic Disease: The Hand", C. B. Wynn Parry, Dec. 1984, p. 693.
"Non-Operative Hand Management of Adult-Onset Rheumatoid Arthritis", Kay Patricia MacBain, et al., 1981, Appendix F.
"Principles of Physical Medicine and Rehabilitation in the Musculoskeletal Diseases", James C. Leek, et al., 1986, p. 108, FIGS. 5-6, p. 109.
"Rehabilitation Management of Rheumatic Conditions", George Ehrlich, M.D., second edition, 1986, pp. 260-261, FIGS. 18.4 and 18.5.
"Rheumatic Disease: Occupational Therapy and Rehabilitation", Jeanne Lynn Melvin, edition 2, 1983, FIG. 95, p. 347.

Primary Examiner—Robert A. Hafer
Assistant Examiner—Kevin G. Rooney
Attorney, Agent, or Firm—W. Brown Morton, Jr.

[57] ABSTRACT

An elliptical finger ring splint comprising two elliptically shaped rings joined at an apex which, when worn, is positioned directly beneath a finger joint when the palm is turned downwards. The tops of the rings are spread such that the planes of the rings form a V, with the top of one ring impinging upon the top of the more distal phalanx of the finger, and the top of the other ring impinging upon the top of the more proximal phalanx, when the finger is fully extended without hyperextension. The rings are made of a rigid but slightly deformable material which in the preferred embodiment is silver or gold to give an attractive appearance while retaining and enhancing the therapeutic orthotic values. The elliptical shapes permit the apex to be positioned directly beneath the finger joint with the rings canted at approximately a 45° angle to the axis of the finger thus impinging upon the tops of the adjacent phalanges urging the finger towards flexion and inhibiting hyperextension. The rings are sized for each individual phalanx to provide lateral stability during all degrees of flexion and extension. They are joined in such a fashion that the apex is slightly deformable thus permitting adjustment of the angle between the planes of the rings for variations in finger size and comfort.

3 Claims, 2 Drawing Sheets

ELLIPTICAL FINGER RING SPLINT

BACKGROUND OF THE INVENTION

1. Field of the Invention

This invention relates to orthopaedic splint type devices used for the therapeutic treatment of instability and hyperextension of the finger joints.

2. Description of the Prior Art

Rheumatoid arthritis is an incurable disease which affects a large number of individuals to varying degrees. In severe cases, the disease is both painful and crippling. Various adaptive equipment and splints exist in the prior art to assist individuals in dealing with the effects of this disease.

When the hands become involved in the arthritic disease process, internal forces in the fingers change due to pain, inflammation and swelling. This creates an imbalance in forces which results in deformities. Specifically, as the tendons and ligaments around the joint become overstretched and the bone structure of the joint deteriorates due to the disease, the joints become very unstable in all directions through the full range of flexion and extension. Chronic pain and general muscle weakness exacerbate the problem of joint instability to the point of serious loss in function of the rheumatoid hand.

Joint instability in the lateral plane frequently results in loss of prehension, ulnar drift and other functional problems.

Joint instability in the flexion-extension plane often results in hyperextension of the finger joints resulting in a deformity called "swan-neck deformity". This condition is characterized by hyperextension of the interphalangeal joints of the finger in the dorsal direction (away from the palm of the hand) substantially more than the approximately 180° extension found in the normal finger.

There are numerous types of finger splints and orthopaedic support devices available in the prior and existing art to prevent the fingers from hyperextending. The closest prior art known to applicant is set forth in the following U.S. Patent:

U.S. Pat. No. 3,170,460 - Stilson: "One-Piece Openwork Finger Splint", patent issued: Feb. 23, 1965.

Additional relevant art which may be prior or subsequent to applicant's invention, but which is approximately contemporaneous is shown in the following U.S. Patents:

U.S. Pat. No. 4,270,528 - Hanson: "Finger Ring Splint", patent issued: June 2, 1981.

U.S. Pat. No. 4,297,992 - LaRue, et al.: "Distal Joint Finger Splint", patent issued: Nov. 3, 1981.

Applicant is an Occupational Therapist who herself has lateral instability and hyperextension of the interphalangeal joints. As such, she has noted in herself and her patients that the finger splints commercially available in the prior art have the following objections to use:

(a) They fail to stabilize the joint in the lateral plane;
(b) They are bulky and uncomfortable to wear and abnormally abduct the fingers (spread the fingers apart);
(c) Finger splints on adjacent fingers interfere with each other;
(d) They are difficult or impossible for the wearer to adjust when the fingers expand and contract with changes in weather, activity and medical condition of the patient; and
(e) They are aesthetically unattractive resulting in low patient compliance in the use of the splints.

The instant invention overcomes these problems and objections by making the splint from two custom fit elliptical rings lying in intersecting planes and with their major axes joined at an apex which, when worn, is positioned immediately under the finger joint. Use of custom fit elliptical rings permits an exact fit of the finger on each side of the interphalangeal joint. The exact fit of the finger and placement of the apex of the rings directly under the joint results in joint stabilization in the lateral plane at all times and through all degrees of flexion and extension.

Prior art does not provide lateral stabilization, but rather the distal phalanx remains unsupported in all positions except full extension. This result necessarily occurs in Hanson (see reference above) because the distal ring joins the proximal ring rearward of the joint and therefore must be large enough to provide clearance for the interphalangeal joint during flexion.

Additionally, elliptical proximal and distal rings permit the use of smaller, more malleable and more yieldable materials such as fine silver and gold to make finger splints which are small in size relative to the prior art, more comfortable to wear, more attractive and more easily adjustable, and are therefore of greater therapeutic value because the patient is more compliant in the use of the prescribed therapeutic (orthotic) device.

SUMMARY OF THE PRESENT INVENTION

In the discussion which follows, the words "ellipse" and "elliptical" are used to refer to a curvilinear, closed, plane figure as opposed to a circle. "Ellipse" as used herein does not include the case of the curvilinear plane figure corresponding to the classic general definition of an ellipse wherein the two focal points coincide thus defining a circle unless the context clearly indicates otherwise.

The subject invention comprises a finger ring splint generally of the nature of finger ring splints already known in the prior art but differing in two important regards. The subject elliptical finger splint consists essentially of two elliptically shaped rings lying in intersecting planes joined together at the point herein called "the apex", where their major axes intersect. The planes of the rings are appropriately perpendicular. Thus the rings are spread apart from the apex so that the ring splint, when viewed in elevation, appears approximately in the shape of a "V" with the apex at the bottom of the "V" and an approximately 90° angle between the sides of the "V". The elliptical finger splint may be made of a suitable metal, plastic or other semi-rigid but deformable material. The preferred embodiments are those made of gold or silver. In any embodiment, however, the finger splint should be only sufficiently deformable that a person, preferably the patient, can without tools spread or close the "V" of the splint to adjust for comfort and changes of finger size due to weather, medical and other conditions. As the "V" is closed, the ring size as measured in a cross-section perpendicular to the axis of the finger effectively increases. The elliptical finger splint is slipped over the patient's affected finger and positioned such that the apex of the "V" is directly under the interphalangeal joint with one ring, the distal ring, extending forwardly (distally) from the apex to the top of the ring, and the second ring, the proximal ring, extending rearwardly (proximally) from the apex to the top of the second ring. In the preferred embodiment, the proximal and distal rings are separately fitted for each individual finger with the distal ring being smaller than the proximal ring. This assures maximum comfort to the patient while keeping the rings as close-fitting as possible in order to maximize their stabilizing effect and therapeutic capability.

DESCRIPTION OF THE PREFERRED EMBODIMENT

Figure 1:
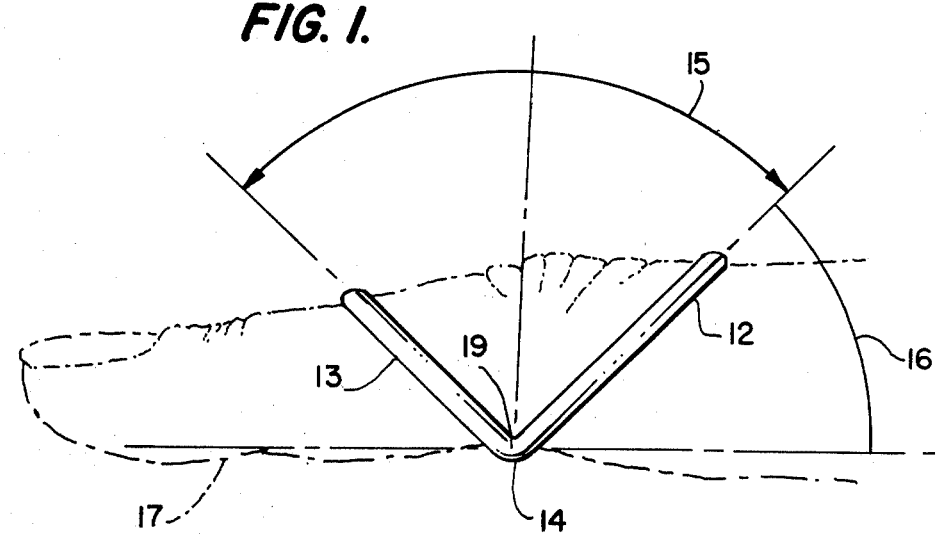
FIG. 1 is a side elevation showing the ring splint, placed upon the finger at the interphalangeal joint.
Figure 2:
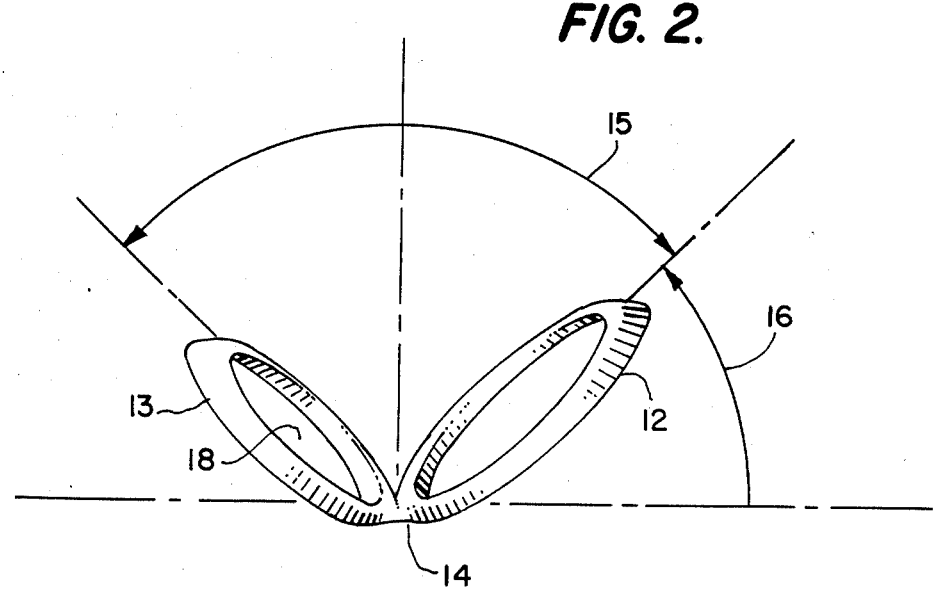
FIG. 2 is a perspective view of the elliptical ring splint of the current invention.
Figure 3:
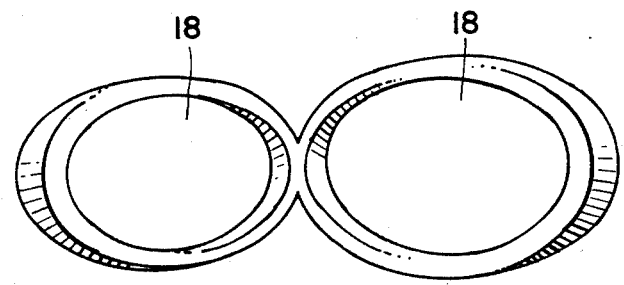
FIG. 3 is a top view of the elliptical ring splint of the present invention.
Figure 4:
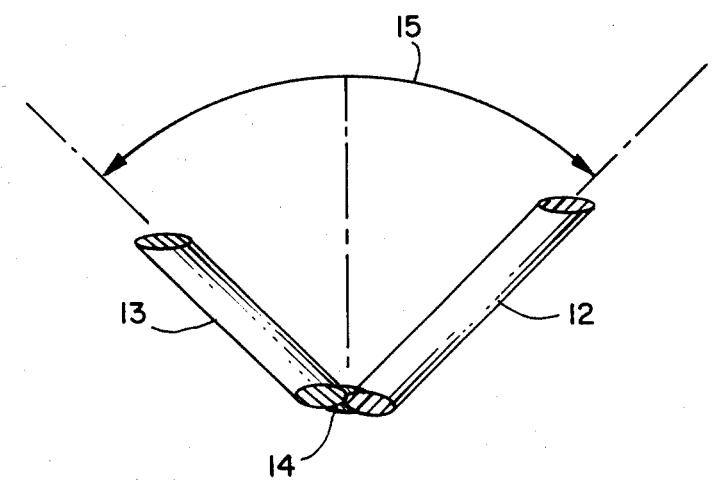
FIG. 4 is a side elevation of the ring splint of the present invention shown in cross-section.

The current invention is generally characterized as a finger splint to stabilize the interphalangeal joint laterally and to inhibit hyperextension resulting from joint instability caused by rheumatoid arthritis or other joint abnormality. The splint is designed to permit flexion (bending the finger towards the palm) with a minimal of interference from the splint while maintaining lateral stability in the joint during bending by securely but comfortably limiting the lateral movement of the finger on both the proximal and distal sides of the joint.

The elliptical ring splint is comprised of two rings 12, 13 which, in the preferred embodiment, are ornamentally manufactured from gold, silver, gold-plated steel or similar material designed to be attractive, ornamental and aesthetically pleasing to the wearer. The rings may be made of plastic or a similar substitute material, but in any event, the ring should be rigid but slightly yieldable.

The rings are elliptical in shape and are joined at an apex 14 located at the intersection of the planes of the two rings (the rings being in planes roughly perpendicular to each other), with the portions of the rings opposite the apex spread apart such that, from the side of the rings, the joined rings form a "V" 15 with the apex at the bottom. The angle 15 between the sides of the "V" (that is, between the planes of the rings) may be varied according to the condition and needs of the individual patient, but optimally is on the order of 90°.

When fitted for use on the ordinary patient, the apex of the splint is placed directly beneath the affected finger joint with one ring (the distal ring) 13 extending forward or distally from the apex to the top, and the second ring (the proximal ring) 12 extending rearwardly or proximally from the apex to the top. When in use, therefore, the angle 16 between the plane of each ring and the longitudinal axis of the finger in normal extension is optimally approximately 45°.

Each ring splint is custom manufactured for each finger of each patient. Measurements are taken by the therapist of the ring size required for each phalanx of the finger which is to receive a ring portion of a finger splint. Thus, in ordinary use, for the proximal interphalangeal joint, for example, the distal ring 13 will be smaller than the proximal ring 12.

The elliptical ring splint of the current invention is shown in use in FIG. 1. In use, the splint is slid over the affected finger 17 such that the opening of the rings 18 receives the finger as the tip of the finger is inserted into the proximal ring 12 first, then through the distal ring 13. The apex of the splint 14 is positioned directly under the center of the interphalangeal joint at the centerline of the joint 19. When properly fit and positioned, the finger is snugly and comfortably supported on each side of the interphalangeal joint during both flexion and extension.

While tendons in the normal hand provide support for the joints and their movement, joint instability is a major problem with the arthritic hand. The inventor has found through experimentation that because of the wider "V" 15 (90°) permitted by the use of elliptical rings, smaller and thinner materials may be used in construction of the rings than was possible with the prior art utilizing a relatively small and thin apex in the splint. The smaller apex 15 is therefore enfolded in the crease of the finger joint when the finger is bent in flexion. Through experimentation and follow-up, the inventor has found that an elliptical ring splint as described herein significantly limits the lateral movement of the phalanges and stabilizes the finger joint. Patients report a high degree of comfort when wearing these new finger splints.

I claim:

1. A finger splint specially adapted both for laterallly stabilizing an interphalangeal joint during flexion and extension and for preventing or inhibiting hyperextension of a finger joint consisting essentially of proximal and distal elliptical rings, said rings being so positioned that their planes intersect and their major axes intersect and lie in a third plane perpendicular to the line of intersection of said first planes, with the rings fixedly but deformably joined at an apex at the intersection of said major axes, the major and minor axes of said proximal ring being longer than those of said distal ring, whereby, said rings are sized according to the wearer's finger dimensions to receive said wearer's affected finger snugly but comfortably with said apex positioned directly under the interphalangeal joint, the distal ring impinging upon the top of the more distal phalanx and with the proximal ring impinging upon the top of the more proximal phalanx when said finger is fully extended without hyperextending.

2. The finger splint of claim 1, wherein said material consists of a precious metal.

3. The finger splint of claim 1, wherein the angle between the planes of the said rings is in the approximate range of 60° to 120°.

* * * * *